US009814677B2

(12) United States Patent
Waldoefner et al.

(10) Patent No.: US 9,814,677 B2
(45) Date of Patent: Nov. 14, 2017

(54) MAGNETIC TRANSDUCERS

(71) Applicant: MagForce AG, Berlin (DE)

(72) Inventors: Norbert Waldoefner, Berlin (DE); Kerstin Stief, Berlin (DE)

(73) Assignee: MAGFORCE AG, Berlin (DE)

(*) Notice: Subject to any disclaimer, the term of this patent is extended or adjusted under 35 U.S.C. 154(b) by 0 days.

(21) Appl. No.: 14/277,904

(22) Filed: May 15, 2014

(65) Prior Publication Data
US 2014/0302154 A1 Oct. 9, 2014

Related U.S. Application Data

(62) Division of application No. 12/738,970, filed as application No. PCT/DE2009/000038 on Jan. 9, 2009, now Pat. No. 8,771,699.

(30) Foreign Application Priority Data

Jan. 9, 2008 (DE) ........................ 10 2008 003 615

(51) Int. Cl.
| | |
|---|---|
| *A61K 9/14* | (2006.01) |
| *A61K 45/06* | (2006.01) |
| *A61K 33/26* | (2006.01) |
| *A61K 41/00* | (2006.01) |
| *B82Y 30/00* | (2011.01) |
| *C01G 49/02* | (2006.01) |
| *C01G 49/06* | (2006.01) |
| *C01G 49/08* | (2006.01) |
| *C09C 1/24* | (2006.01) |

(52) U.S. Cl.
CPC .............. *A61K 9/143* (2013.01); *A61K 33/26* (2013.01); *A61K 41/0052* (2013.01); *A61K 45/06* (2013.01); *B82Y 30/00* (2013.01); *C01G 49/02* (2013.01); *C01G 49/06* (2013.01); *C01G 49/08* (2013.01); *C09C 1/24* (2013.01); *C01P 2004/42* (2013.01); *C01P 2004/64* (2013.01)

(58) Field of Classification Search
None
See application file for complete search history.

(56) References Cited

U.S. PATENT DOCUMENTS

| | | | | |
|---|---|---|---|---|
| 3,945,945 | A | 3/1976 | Kiovsky et al. | |
| 3,947,502 | A | 3/1976 | Leitner et al. | |
| 4,169,912 | A | 10/1979 | Schönafinger et al. | |
| 4,271,234 | A | 6/1981 | Schönafinger et al. | |
| 4,744,802 | A | 5/1988 | Schwabel | |
| 5,034,145 | A | 7/1991 | Leising et al. | |
| 5,460,831 | A | 10/1995 | Kossovsky et al. | |
| 5,462,751 | A | 10/1995 | Kossovsky et al. | |
| 5,547,748 | A | 8/1996 | Ruoff et al. | |
| 5,593,781 | A | 1/1997 | Nass et al. | |
| 5,616,311 | A | 4/1997 | Yen | |
| 5,718,907 | A | 2/1998 | Labarre | |
| 5,922,403 | A | 7/1999 | Tecle | |
| 5,922,537 | A | 7/1999 | Ewart et al. | |
| 6,022,500 | A | 2/2000 | John et al. | |
| 6,045,821 | A | 4/2000 | Garrity et al. | |
| 6,103,379 | A | 8/2000 | Margel et al. | |
| 6,183,658 | B1 | 2/2001 | Lesniak et al. | |
| 6,541,039 | B1 | 4/2003 | Lesniak et al. | |
| 8,771,699 | B2 | 7/2014 | Waldoefner et al. | |
| 2006/0211152 | A1 | 9/2006 | Peng et al. | |
| 2008/0187595 | A1* | 8/2008 | Jordan et al. | 424/490 |
| 2009/0317408 | A1* | 12/2009 | Ivkov | A61K 41/0052 424/178.1 |
| 2011/0177153 | A1 | 7/2011 | Zhu | |

FOREIGN PATENT DOCUMENTS

| | | | |
|---|---|---|---|
| DE | 25 43 962 | A1 | 4/1977 |
| DE | 196 14 136 | A1 | 10/1997 |
| DE | 102 61 406 | A1 | 7/2004 |
| EP | 0 200 487 | A2 | 5/1986 |
| EP | 0 472 990 | B1 | 3/1992 |
| EP | 0 667 148 | A1 | 8/1995 |
| JP | 5-277355 | A | 10/1993 |
| JP | 6-270155 | A | 9/1994 |
| JP | 52-44794 | | 4/1997 |
| JP | 2000-509005 | | 7/2000 |
| KR | 20040034224 | A * | 4/2004 |
| RU | 2089507 | C1 | 10/1997 |
| RU | 2291880 | C1 | 1/2007 |
| WO | WO-88/00060 | A1 | 1/1988 |
| WO | WO-90/01295 | A1 | 2/1990 |
| WO | WO-90/03838 | A1 | 4/1990 |
| WO | WO-93/24076 | A1 | 12/1993 |
| WO | WO-96/02060 | A1 | 1/1996 |
| WO | WO 97/38058 | | 10/1997 |
| WO | WO-98/40049 | A2 | 9/1998 |
| WO | WO-98/58673 | A1 | 12/1998 |
| WO | WO-2006/057533 | A1 | 6/2006 |
| WO | WO-2006/108405 | | 10/2006 |
| WO | WO-2006/125452 | A1 | 11/2006 |

OTHER PUBLICATIONS

Wu, Wei; He, Quanguo; Jiang, Changzhong. "Magnetic Iron Oxide Nanoparticles: Synthesis and Surface functionalization strategies" Nanoscale Research Letters, 2008, v. 3, pp. 397-415.*

(Continued)

*Primary Examiner* — Mina Haghighatian
*Assistant Examiner* — Erin Hirt
(74) *Attorney, Agent, or Firm* — The Marbury Law Group, PLLC (57) ABSTRACT

Embodiments herein relate to the production of biocompatible magnetic nanoparticles with a high SAR-value which produce a large amount of heat when exposed to an alternating magnetic field. The produced heat can be used among others for therapeutic purposes, in particular for combating cancer.

19 Claims, 3 Drawing Sheets

(56) References Cited

OTHER PUBLICATIONS

Basu, S. et al., "Conductivity relaxation in the interfacial phase of iron core-iron oxide shell nanocomposites", J. Mater. Res., vol. 21(7),1704-1711 (2006).

DePalma et al. "Surface Modification of γ-$Fe_2O_3$@$SiO_2$ Magnetic Nanoparticles for the Controlled Interaction with Biomolecules", Journal of Nanoscience and Nanotechnology; vol. 7; pp. 4626-4641 (2007).

De Palma, R. et al., "Silane Ligand Exchange to Make Hydrophobic Superparamagnetic Nanoparticles Water-Dispersible," Chem. Mater., (2007), vol. 19, No. 7, pp. 1821-1831.

Gupta, A. K. et al., "Synthesis and surface engineering of iron oxide nanoparticles for biomedical applications," Biomaterials, (2005), vol. 26, 3995-4021.

Hermentin, P. et al., "Hinge-Thiol Coupling of Monoclonal Antibody to Silanized Iron Oxide Particles and Evaluation of Magnetic Cell Depletion," Bioconjugate Chem., (1990), vol. 1, No. 6, pp. 411-418.

Jordan, A. et al., "Inductive heating of ferrimagnetic particles and magnetic fluids: physical evaluation of their potential for hyperthermia," International Journal of Hyperthermia, (1993), vol. 9, No. 1, pp. 51-68.

Jung, C. W. et al., "Physical and Chemical Properties of Superparamagnetic Iron Oxide MR Contrast Agents: Ferumoxides, Ferumoxtran, Ferumoxsil," (1995), Magnetic Resonance Imaging, vol. 13, No. 5, pp. 661-674.

Kim, D. K. et al., "Synthesis and characterization of surfactant-coated superparamagnetic monodispersed iron oxide nanoparticles", Journal of Magnetism and Magnetic Materials, (2001), 225, 30-36.

Santra et al., "Synthesis and characterization of silica-coated iron oxide nanoparticles in microemuision: the effect of nonionic surfactants", Langmuir, vol. 17, (2001) pp. 2900-2906.

Smith, T. W. et al., "Colloidal Iron Dispersions Prepared via the Polymer-Catalyzed Decomposition of Iron Pentacarbonyl," J. Phys. Chem., (1980), vol. 84, 1621-1629.

Steitz, B. et al., "Production and Biofunctionalization of Magnetic Nanobeads for Magnetic Separation of Messenger RNA", Biophysical Reviews and Letters, vol. 2, No. 1, 2007, 109-122.

Sun, S. et al., "Monodisperse $MFe_2O_4$ (M=Fe, Co, Mn) Nanoparticies," J. Am. Chem. Soc., (2004) vol. 126, No. 1, pp. 273-279.

Wang, Y. et al., ""Pulling" Nanoparticles into Water: Phase Transfer of Oleic Acid Stabilized Monodisperse Nanoparticles into Aqueous Solutions of α-Cyclodextrin," Nano Letters, (2003), vol. 3, No. 11, pp. 1555-1559.

Yuan et. al., "Surfactant mediated nanoparticle assembly of catalytic mesoporous crystalline iron oxide materials", Catalysis Today, (2004), v 93-95, pp. 743-750.

Zablotskaya, A. et al., "Synthesis and characterization of nanoparticles with an iron oxide magnetic core and a biologically active trialkylsilylated aliphatic alkanolamine shell," Journal of Magnetism and Magnetic Materials, (2007) vol. 311, pp. 135-139.

Hyeon, T., et al. (2001). "Synthesis of Highly Crystalline and Monodisperse Maghemite Nanocrystallites without a Size-Selection Process." Journal of the American Chemical Society 123(51): 12798-801.

Hyeon, T. (2003). "Chemical synthesis of magnetic nanoparticles." Chemical Communications (8): 927-34.

Park, J., et al. (2004). "Ultra-large-scale syntheses of monodisperse nanocrystais." Nat Mater 3(12): 891-5.

Wang, L., et al. (2006). "One-pot synthesis and bioapplication of amine-functionalized magnetite nanoparticles and hollow nanospheres." Chemistry 12(24): 6341-7.

* cited by examiner

MAGNETIC TRANSDUCERS

BACKGROUND OF THE INVENTION

1. Field of the Invention

The present invention relates to the production of biocompatible magnetic nanoparticles which produce a large amount of heat when exposed to an alternating magnetic field. The produced heat can be used e.g., for therapeutic purposes, in particular for combating cancer.

2. Description of the Relevant Art

Magnetic nanoparticles can convert the energy of a magnetic field into heat in various ways. Besides the heating through so-called hysteresis losses nanoparticles can generate heat through relaxation (Néel and Brown relaxation, respectively). The amount of the produced thermal energy depends on the magnetic field strength (amplitude) and the frequency of the alternating field. The efficiency of the heat production can, at defined strength and frequency of the magnetic field, be estimated by the so-called SAR (specific absorption rate) or SLP (specific power loss) values. SAR values of a substance are normalized to the mass (in grams) used for the measuring and are expressed in the unit [W/g]. However, the SAR value of a magnetic substance depends yet on other factors, such as the particle size and the particle form, the anisotropy and the metal content of the substance. The SAR is preferably determined according to a method developed by Jordan et al. [International Journal of Hyperthermia, 1993, Vol. 9, No. 1, 51-68] at a frequency of 100 kHz and a field strength of up to 18 kA/m. Here, the SAR value is indicated by a normalization on the iron content of the substance in mW/mg Fe.

Biocompatible magnetic nanoparticles are frequently produced by a so-called precipitation process. This is described by many examples in literature [e.g. DE 196 14 136 A1]. Since these particles are produced in aqueous solution, they can be functionalized without problems and usually possess a good biocompatibility. The particles produced this way show, however, relatively low SAR values and can therefore not meet the innovative requirements of this patent.

Magnetic nanoparticles can also be produced by so-called magnetotactic bacteria [WO 98/40049]. The nanoparticles produced this way have a higher SAR. However, the production process is very complex and expensive. In addition the particles sediment relatively fast, thereby strongly limiting the possible applications.

It is known for years that thermal decomposition of metal complexes in organic solvents results in the formation of colloids or nanoparticles [e.g. Smith et al., J. Phys. Chem. 1980, 84, 1621-1629]. Monodisperse particles of different sizes can be produced by the method published by Pen et al. [US 2006/0211152 A1] and Hyeon et al. [WO 2006/057533 A1]. However, the particles produced by this method are dispersible in organic solvents only and therefore not biocompatible. Furthermore, the SAR values of the particles produced by this method are low. The dispersion of such (hydrophobic) particles in water can be principally achieved by a modification of the shell [e.g. Wang et al, Nano Lett., 2003, 3(11), 1555-1559 or De Palma et al., Chem. Mater, 2007, 19, 1821-1831]. These methods are based on the direct exchange of hydrophobic ligands through hydrophilic ligands. These coating methods result in only a thin (monolayer) coating which does not meet the requirement of a stable biocompatible coating. Furthermore, the colloidal stability of the particles is limited, so that the particles cannot be coated with this method. Further, only highly diluted dispersions of the particles can be coated. Thus, no satisfying technical solution for the dispersion of the particles exists on industrial scale. Further, the substances or solvents used for the dispersion usually possess a high toxicity, thus limiting the biocompatibility.

Biocompatible iron oxide nanoparticles can also be obtained by a coating with silanes according to DE 196 14 136 A1, however, this method is applicable only when the particles are already dispersed in water, whereas hydrophobic particles cannot be readily coated with silanes or silica.

SUMMARY OF THE INVENTION

In an embodiment, biocompatible magnetic nanoparticles with a high SAR value in an alternating magnetic field include a coating of a stable, silicon-containing shell with a thickness ranging from 0.5 to 10 nm, preferably 1 nm to 6 nm and more preferably 3 nm. The strength of the alternating magnetic field used for the determination of the SAR ranges preferably between 3 and 18 kA/m and the frequency ranges between 1 kHz and 100 MHz and preferably between 10 and 1000 kHz.

The described task is solved by the production method according to claim 1, the nanoparticles according to claim 26 and the pharmaceutical composition according to claim 28, and the use of the nanoparticles according to claim 31.

Further advantageous embodiments result from the dependent claims, the examples, the figures and the description.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
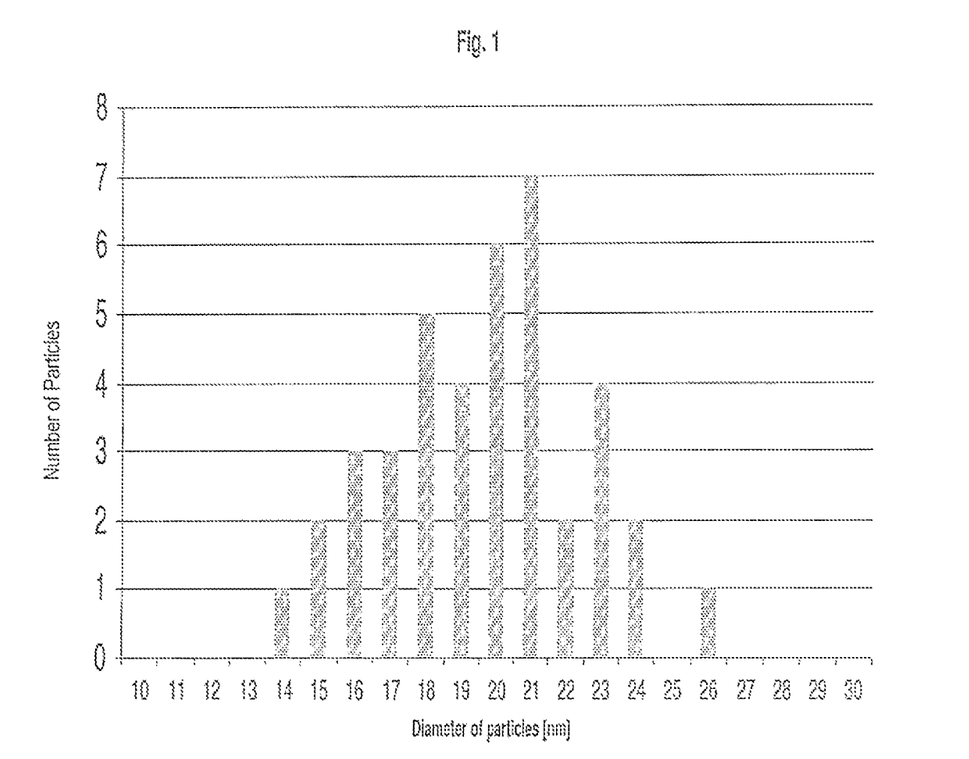
FIG. 1 shows the particle size distribution (derived from transmission electron microscopy images) of inventive iron oxide nanoparticles.
Figure 2:
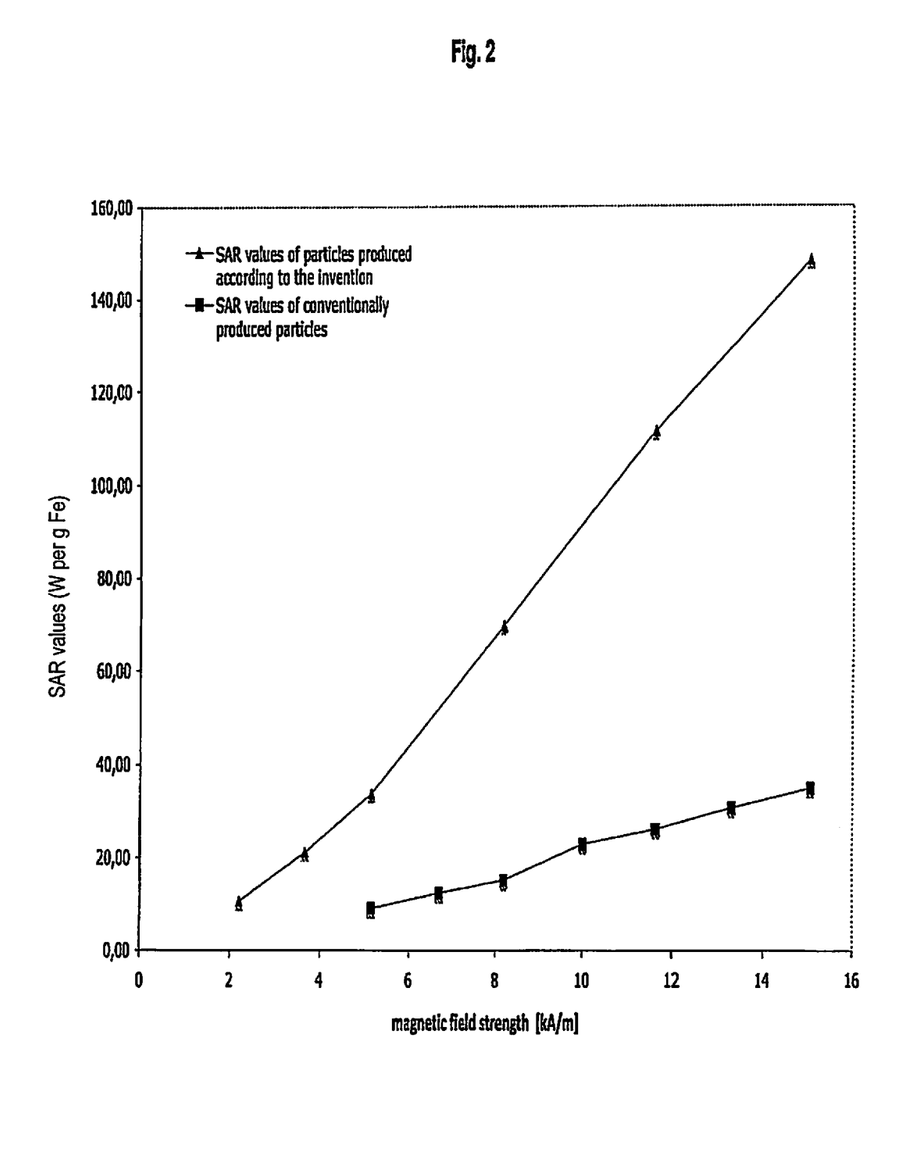
FIG. 2 shows the SAR values of inventive iron oxide nanoparticles in water compared to the SAR values of conventional iron oxide nanoparticles, manufactured by a precipitation according to patent specification DE19614136A1. The SAR values refer to an alternating magnetic field with a frequency of 100 kHz.
Figure 3:
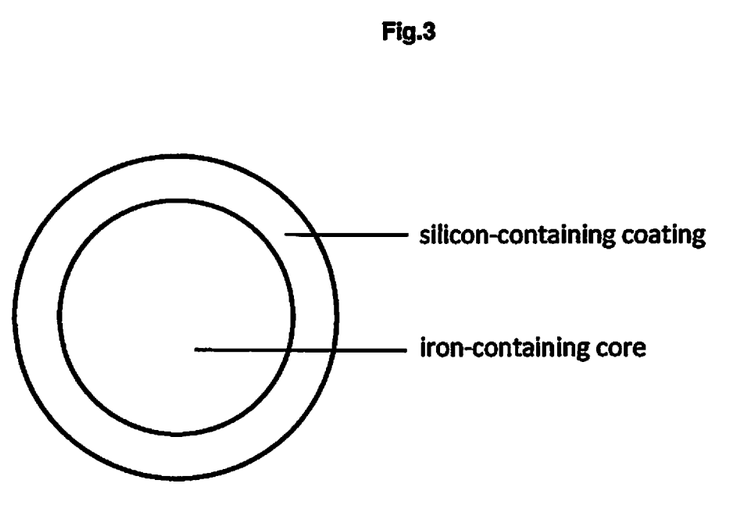
FIG. 3 shows a schematic representation of the inventive iron-containing nanoparticles with core and shell.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

In an embodiment, biocompatible nanoparticles include a stable, silicon-containing shell, which has a preferred thickness ranging from 0.5 to 10 nm, more preferably from 1 nm to 6 nm, still more preferably from 2 nm to 4 nm and most preferably from 3 nm, and which has a high SAR value in an alternating magnetic field, wherein the strength of the alternating magnetic field is preferably between 3 and 18 kA/m and wherein the frequency is preferably between 10 and 1000 kHz.

In an embodiment, particles with a high SAR value can be produced by a method comprising:
- A1) Providing a composition of at least one iron-containing compound A in at least one organic solvent LM1;
- B1) Heating the composition at a temperature in the range of 50° C. to a temperature of 50° C., below the actual reaction temperature of the iron-containing compound A according to step C1 for at least 10 minutes;
- C1) Heating the composition up to a temperature between 200° C. to 400° C.;
- D1) Purification of the obtained particles;
- E1) Suspending of the purified nanoparticles in water or an aqueous solution of an acid;
- F1) Addition of a surface active compound to the aqueous solution obtained according to step E1);
- G1) Treatment of the aqueous solution according to step F1) with ultrasound;
- H1) Purification of the aqueous dispersion of the particles obtained according to step G1);
- I1) Production of a dispersion of the particles according to step H1) in a solvent mixture comprising water and a solvent miscible with water,
- J1) Addition of an alkoxysilane to the dispersion of the particles in the solvent mixture according to step I1),
- K1) Purification of the particles.

The steps A1 to K1 usually follow one another, wherein an additional step A2 can take place after step A1 and before step B1 and/or an additional step B2 can take place after step B1 and before step C1. Likewise, after step C1, D1, E1, F1, G1, H1, I1, J1 or K1 can optionally follow an oxidation step C2, D2, E2, F2, G2, H2, I2, J2 or K2. Herein, the step C2, D2, E2, F2, G2, H2, I2, J2 or K2 is also designated as step X2. The additional steps A2, B2 and/or X2 are optional and not essential for the performance of the invention.

Further it is part of the average proficiency of a person skilled in the art to adapt and to optimize the reaction parameters depending on the chosen reaction temperature or on the chosen iron-containing compound A or on the chosen other components. For example, the duration of the heating period B1 of the respective reaction can be optimized by a person skilled in the art in a way that particles with a maximal SAR are formed. The duration of the minimum heating period is 10 minutes; it is obvious to a person skilled in the art that the heating period becomes shorter with rising temperature. Likewise, the heating rate, the final temperature and the holding time of the final temperature in step C1 can be adapted by a person skilled in the art in a way that particles with a maximum SAR are formed.

The particles are preferably nanoparticles, meaning particles with a diameter in the nanometer range, wherein microparticles may also be obtained according to the inventive method.

The used iron-containing compounds A or the used iron-containing compound A will be preferably selected from the group comprising or consisting of iron complex compounds, iron carbonyl compounds, iron salts, particularly iron salts of saturated or unsaturated fatty acids, organic iron compounds, and iron-sandwich-complexes.

As iron carbonyl compounds can be named iron dicarbonyl $(Fe(CO)_2)$, iron tetracarbonyl $(Fe(CO)_4)$ or iron pentacarbonyl $(Fe(CO)_5)$, and examples of iron salts are iron dichloride, iron dibromide, iron difluoride, iron diiodide, iron trichloride, iron tribromide, iron trifluoride, iron triiodide, iron(II) sulfate, iron(III) sulfate, iron acetate, iron oxalate, iron(II) nitrate, iron(III) nitrate, iron carbonate, iron(II) hydroxide, iron(III) hydroxide, iron phosphate, triiron diphosphate. Ferrocene is an example for an iron-sandwich-complex, and iron acetyl acetonate is an example for an iron complex compound. As metal organic iron compounds are considered e.g. iron(II) acetate, iron(III) acrylate, iron(III) oleate, iron alkoxides such as iron(III) ethoxide, or also iron carbonyl compounds such as acetyl-cyclobutadiene-iron-tricarbonyl, butadiene-iron-tricarbonyl and olefin-iron-tetracarbonyl.

As organic solvent LM1 all high boiling solvents can be used. Preferred are solvents of the group comprising or consisting of: high boiling amines, alkanes, olefins, alcohols or ethers. Furthermore, monoethers and diethers of dioles (alkandioles) as well as monoethers, diethers, triethers of trioles (alkantrioles), alkylene-glycol-monoethers, alkylene-glycol-diethers, ethylene-glycol-monoether, ethyleneglycol-diether, propylene-glycol-monoether, propylene-glycol-diether, glycerin-monoether, glycerin-diether, glycerin-triether, and glycol-diether (glymes) can be used. The solvent L2 can also be selected from the group mentioned above.

Particularly preferred solvents LM1 as well as LM2 are glycol-diethers (also called "glymes") with a minimum boiling point of 200° C. For the production of nanoparticles from iron salts (e.g. chlorides) ethylene glycol is also suitable. Basically, the boiling point of the solvent should be higher than 150° C., further preferred higher than 175° C. and particularly preferred higher than 200° C.

The at least one iron-containing compound A is dispersed, dissolved or suspended in the solvent LM1 and the obtained composition is then heated to a temperature in the range from 50° C. to a temperature of 50° C. below the actual reaction temperature of the iron-containing compound A according to step C1 for a minimum period of 10 minutes. The actual reaction temperature is understood as the temperature for the particle formation, which ranges between 200° C. and 400° C. Thus, the temperature of the nucleation according to step B1 ranges between 50° C. and a maximum of 350° C., however, always at least 50° C. below the temperature according to step C1. Thus, the heating of one or more iron-containing compounds A in the organic solvent LM1 or in the mixture of organic solvents LM1 is preferably carried out at a temperature of about 50° C. below the actual temperature for the particle formation of the compound A according to step C1.

This heating phase prior to particle formation according to step B1) is used for the formation of so called seeds, which thereafter enable a defined particle formation. The time period of the heating phase has a large influence on the SAR of the resulting particles, preferably nanoparticles, generated in step C1). For producing particles or nanoparticles, with a high SAR value the reached temperature is kept for a minimum period of 10 minutes, preferably for a minimum period of 30 minutes and particularly preferably for a minimum period of about 40 minutes. Thus, a composition of at least one iron-containing compound A and at least one solvent LM1 should be heated to the above-specified temperature for preferably 30 to 50 minutes.

Depending on the used iron-containing compound A a temperature is preferably aimed at which is about 100° C. to 300° C., preferably about 130° C. to 270° C., more preferred about 150° C. to 250° C., still more preferred about 170° C. to 230° C., still more preferred 180° C. to 220° C., still more preferred about 190° C. to 210° C. and particularly preferred about 200° C. below the actual reaction temperature for particle formation according to step C1), wherein the aimed temperature is not below 70° C., preferably not below 90° C. and particularly preferably not below 100° C. Preferably, the temperature during the first heating phase will be kept at 100° C. to 150° C., according to step B1).

To influence or to promote the seed formation, additives or surface-active compounds can be added according to step A2). The terms "additive" or "surface-active compound" as used herein stand in the context that most additives are also surface-active compounds, which is however not necessarily the case for all additives. Therefore, every surface-active compound can be referred to as an additive, wherein, however, not every additive can be referred to as a surface-active compound. This includes tensides, silanes, Si- or Al-containing organic compounds, phosphines, saturated or unsaturated fatty acids, amines, diamines, carboxylic acids and salts thereof; saturated and unsaturated fatty acids, or also polymers. Examples for polymers are polyvinyl alcohol, polyethylene glycol, polyacrylic acid, dextran, PLGA, chitin, fibrin, heparin, chitosan and polyethylene imine.

After the healing phase according to step B1) the actual particle formation is performed in step C1). The particle seeds formed in step B1) are heated up to 500° C., however, preferably to a temperature ranging from 200° C. and 400° C.

Thereby iron-containing particles, preferably the iron-containing nanoparticles, are formed from the particles seeds and the excess iron-containing compound A.

It has been shown to be advantageous to start and to carry out the heating phase according to B1) not with the whole amount of the iron-containing compound A, but to add a further iron-containing compound B in an organic solvent L2 in a step B2) after the seed forming step according to B1).

The at least one iron-containing compound B can be selected herein from the above-mentioned group of iron-containing compounds can and be identical to or different from the at least one iron-containing compound A.

The same applies for the organic solvent L2 which can be selected from the above-mentioned group of solvents LM1, and is identical to or different from the solvent LM1, wherein it is preferred if the solvents LM1 and LM2 are identical.

Thus it is preferred if after the seed forming step B1) new iron-containing compound B is added in preferably the same solvent (LM1=LM2) and the composition obtained thereby according to C1) is heated to a temperature up to 500° C., preferably in the range of 200° C. to 400° C. LM1 and LM2 have preferably a minimum boiling point of 200° C.

Hereby the actual particles are produced after addition of the at least one iron-containing compound B in solvent L2. Together with the iron-containing compound B further additives can also be added to the composition obtained after step B1. These additives either do not have to be selected mandatorily from the same additives which are already present in the solution, however, this is preferred.

Here, too, the amount of the added iron-containing compound B, of the additives, and the kind and amount of solvent L2 can be adapted by a person skilled in the art again in such a way that particles with a maximum SAR are formed.

As already set forth, the total amount of the required iron-containing compound can however be added in step A, so that step B2) is preferred, but not mandatory. Even if no further iron-containing compound B is added anymore after the first heating phase according to step B1), a further additive can be added as step B2), which should be the same as the additive already present in the composition. Thus, as step B2) additive only or iron-containing compound B only or both of them simultaneously or sequentially can be added as step B2).

The duration of the second heating phase according to step C1) is at least 30 minutes, preferably 1-30 hours, more preferably 10-20 hours and particularly preferred 15 hours.

Surprisingly, it has become apparent that the SAR can be further increased by elongation of the heating phases or simply by longer heating phases, so that long heating phases and particularly the additional tempering phases are preferred. Particularly in step C1) a heating phase is preferred which is longer than 10 hours, and more preferred longer than 14 hours.

The tempering phases following optionally after step D1 as D1* and/or D2* can increase the SAR further as well, and are therefore preferably also longer than 10 hours, more preferably longer than 14 hours and particularly preferably more than 18 hours. Thus, a tempering phase can take 1-30 hours, preferably 10-25 hours, more preferably 13-22 and particularly preferably 15-20 hours.

The SAR of the resulting particles can be adapted by variation of the duration of the heating phase B1), by the final temperature and by the holding duration of the final temperature in step C1), and by the amount of added iron compounds or additives in step C1), so that particles with a maximum BAR are formed. These parameters depend on the kind of the used iron compounds and the kind of the solvent and the additives. Hence, the heating phases have to be adapted to every system, which can be carried out easily by a skilled person based on his specific knowledge.

The SAR of the inventive particles produced is between 10-40 W per g Fe at a magnetic field strength of 4 kA/m, preferably between 20-40 W per g Fe at a magnetic field strength of 4 kA/m, more preferred between 25-40 W per g Fe at a magnetic field strength of 4 kA/m and particularly preferred between 30-40 W per g Fe at a magnetic field strength of 4 kA/m and a frequency of the alternating magnetic field of 100 kHz.

In the following are provided some examples for systems for the production of inventive particles as well as the SAR values of the produced particles. The examples (I) to (VIII) result in inventive particles with SAR values of 20-40 W per g Fe at a magnetic field strength of 4 kA/m and a frequency of the alternating magnetic field of 100 kHz. The term "Fe" refers to a total iron amount of $Fe^0$, $Fe^{+2}$, $Fe^{+3}$.

TABLE 1

Examples for suitable components for the production of particles

| Iron-containing compound A | Solvent LM1 (Boiling point) | Examples of additives | SAR [W/g Fe] |
|---|---|---|---|
| Iron pentacarbonyl | Diethylene glycol-dibutyl ether (256° C.) | Fatty acids, tensides | 10-30 |
| Iron pentacarbonyl | Dioctyl ether (287° C.) | Fatty acids, tensides | 10-30 |
| Ferrocen | Diethylene glycol dibutyl ether (256° C.) | Fatty acids, tensides, amines | 10-30 |
| Iron acetyl acetonate | Trioctyl amine (365° C.) | Fatty acids, tensides, amines | 15-30 |
| Iron acetyl acetonate | Ethylene glycol (197° C.) | Diamines, carboxylic acids, polymers without additive | 15-30 |
| Iron acetyl acetonate | Triethylene glycol (291° C.) | Diamines, carboxylic acids, polymers without additive | 15-30 |

TABLE 1-continued

Examples for suitable components for the production of particles

| Iron-containing compound A | Solvent LM1 (Boiling point) | Examples of additives | SAR [W/g Fe] |
|---|---|---|---|
| Iron(III) oleate | Polyglycol DME 500 (>250° C.) | Fatty acids, tensides without additive | 15-35 |
| Iron(III) oleate | Trioctyl amine (365° C.) | Fatty acids, tensides | 15-35 |
| Iron(II) oleate | Polyglycol DME 500 (>250° C.) | Fatty acids, tensides without additive | 15-30 |
| Iron(II) oleate | Trioctyl amine (365° C.) | Fatty acids, tensides | 15-35 |
| Iron(III) chloride | Ethylene glycol (197° C.) | Diamines, carboxylic acids, polymers without additive | 20-40 |
| Iron(III) chloride | Triethylene glycol (291° C.) | Diamines, carboxylic acids, polymers | 20-35 |
| Iron(III) ethoxid | Polyglycol DME 500 (>250° C.) | Diamines, carboxylic acids, polymers without additive | 10-25 |

In the afore-mentioned table 1, "without additive" means that the synthesis has been carried out with the components named in the respective column but without the addition of an additive. The components mentioned in table 1 were used according to example 1 and 3A or 2 and 3A (steps A1 to C2), and then all systems were further used according to examples 4-6 as well as 4-7. It has been shown by the application of an additional tempering phase (Example 7; step D1* or D2*) that the SAR could be increased by about 5 W/g Fe at about 5 kA/m. The SAR values shown in table 1 refer to a magnetic field strength of 4 kA/m and a frequency of the alternating field of 100 kHz.

TABLE 2

Examples of systems

| Step | Example (I) | Example (II) | Example (III) | Example (IV) |
|---|---|---|---|---|
| A1 | Fe(III) chloride + ethylene glycyol | Fe(III) chloride + ethylene glycyol | Fe(III) chloride + ethylene glycyol | Fe(III) chloride + ethylene glycyol |
| E1 | Hydrochloric acid | Nitric acid | Hydrochloric acid | Hydrochloric acid |
| F1 | Sodium oleate | cis-11-eicosenic acid (Na-Salt) | Sodium oleate | Sodium oleate |
| I1 | Ethanol/water | Ethanol/water | Isopropanol/water | Isopropanol/water |
| J1 | Tetraethoxy silane | Tetraethoxy silane | Tetraethoxy silane | Bis(Triethoxy silyl) ethane |

| Step | Example (V) | Example (VI) | Example (VII) | Example (VIII) |
|---|---|---|---|---|
| A1 | Fe(III) chloride + ethylene glycyol | Fe(III) oleate + trioctyl amine | Fe(III) oleate + diethylene glycol dibutyl ether | Eisen(III) acetyl acetonate + triethylene glycol |
| E1 | Hydrochloric acid | Hydrochloric acid | Nitric acid | Hydrochloric acid |
| F1 | Sodium oleate | Cis-11-Octadecenic acid (Na-Salt) | Sodium oleate | Sodium oleate |
| I1 | Isopropanol/water | Ethanol/water | Ethanol/water | Isopropanol/water |
| J1 | Tetraethoxy silane | Tetraethoxy silane | Tetraethoxy silane | Bis(Triethoxy silyl) octane |

The phases A) and C) can be carried out optionally under normal pressure at the air or under protective gas atmosphere (argon, nitrogen) or in a reaction autoclave under pressures of up to 400 bar.

After this second heating phase according to step C1) an oxidation phase X2) can follow. The oxidation phase X2) is optional and does not mandatorily have to follow directly after step C1, but can take place also after one of the steps C1) to K1). The particles are herein oxidized preferably by conduction of atmospheric oxygen. The conduction of atmospheric oxygen is performed for 4 to 24 hours, preferably 8 to 16 hours and further preferably at 20° C. to 50° C. However, other volatile oxidation agents or oxidation agents removable by distillation such as oxygen (pure), hydrogen peroxide or other organic oxidation agents such as amine oxides can be used also. Thus, it is preferred if after one of the steps C1) to K1) follows an oxidation step X2), wherein X is a variable for the letters C to K, depending on after which step the oxidation is performed. Should the optional oxidation be performed after step E1) the oxidation is referred to as step E2), and should it be performed after K1, the oxidation step will be referred to as K2). Further, the oxidation step can be repeated multiple times or a further oxidation step X2' can follow after a further procedural step, which is possible but not preferred. Therefore, a method may include a first oxidation step X2 (e.g. F2) and a second oxidation step X2' (e.g. H2'). For particles which are already in a partly or completely oxidized condition, a further oxidation is of course not necessary. Usually, oxidations under atmospheric air are self-starting, so that an additional, i.e. an oxidation step X2 additional to the self-starting oxidation is not necessary. An oxidation step X2 can be carried out even if it is not absolutely necessary because it has been shown that it does not harm either.

The particles, preferably nanoparticles, formed according to step C1, need to be purified. The step improves the quality of products obtained. The use of unpurified particles does not produce particles with a good dispersibility in water and eventually a high SAR. This purification is performed according to step D1) preferably by a Soxhlet extraction, until a dispersibility of the particles in nonpolar solvents is not given anymore. As surprisingly has been found, it is essential for the later dispersion in water [step F1)] that the additive and particularly the surface active compound from step A2) and/or B2) are—as far as possible—completely washed off the particles, i.e. largely removed again. Under the terms "as far as possible" and "largely", respectively, is understood a removal of the additives in the range of 70-100%, preferably up to 90%. Thus, the additives will be removed from the particles by more than 70%, preferably by more than 80%, more preferably by more than 90% and particularly preferably by more than 95%. The afore-mentioned percentages are referred to the additive adhering to the particles. Free additive, i.e. additive swimming freely in the solution and being not adsorbed by the particles can largely be removed by centrifugation, i.e. by >95%, preferably by >98%. The amount of remaining additive adhering to the particles can be determined, for example, by elementary analysis or IR spectroscopy. The percentage is referred herein to the weight (% by weight). The additive not adhering to the particles is removed by centrifugation and the additive adhering to the particles can be preferably achieved by a Soxhlet extraction of the formed particles, wherein an extraction supported by ultrasound can be used also. For this use the nanoparticles will first be separated by centrifugation before the next purification step ensues.

The solvent used for the Soxhlet extraction may be a current polar organic solvent such as alcohols, ketons, ethers or esters. Aceton, ethyl acetate or ethanol are preferred.

The duration of the extraction is between 1 and 8 hours, preferably between 2 and 6 hours and particularly preferably about 4 hours. The crucial point is that the iron-containing particles, preferably nanoparticles, are not dispersible anymore in nonpolar solvents, such as toluol, xylol or hexane, after the extraction. Should this, however, be the case, the extraction time has to be adjusted. The powder of nanoparticles purified that way is dried under vacuum conditions.

Several "tempering phases" can follow after step D1 to increase the crystallinity of the particles. These tempering phases can be carried out in high boiling solvents at up to 400° C. for several hours. Solvents are referred to as high boiling if they have a minimum boiling point of 200° C., preferably of 300° C. The tempering process can take place herein at the air or under protective gas (e.g. argon). At temperatures of about 200° C. to 250° C. the reaction is preferably performed without protective gas, and at temperatures higher than about 200° C. to 250° C. the reaction is preferably performed under protective gas. Alternatively, nanoparticles can be tempered as a powder (without solvents) at temperatures of up to 1000° C. under protective gas. Preferred protective gases are argon or $CO_2/H_2$ mixes. This at least one tempering step follows as a step D1* after step D1 or as D2* after oxidation step D2.

The oxidation according to step X2 with X=C or D or E or F or G or H or I or J or K can preferably be carried out by suspending the particles in 0.5 to 2M $HNO_3$, preferably 1M $HNO_3$, addition of $Fe(NO_3)_3$ and successive boiling underreflux. The ratio of $Fe(NO_3)_3$ to $FeO_x$ or in general the ratio of Fe(III) to Fe % is preferably 1:2. This oxidation process has an advantageous effect on the SAR of the particles and is therefore preferred. It should be noted that this step is not limited to $Fe(NO_3)_3$ and that other Fe(III) salts can also be used, such as $FeCl_3$, $FePO_4$ etc. Now the dispersion of the purified particles or nanoparticles is performed in water by reversible coating with a surface-active compound according to steps E1) and F1).

At this step the purified powder of the particles or nanoparticles is suspended in water, wherein a hydrophilic layer is docked that way that a later removal of this layer is easily possible. At the beginning, the solids content (iron oxide) for this coating is set at preferably 2-20%, more preferably at 3-12%, still more preferably 5%-8%, still more preferably 6%-7% and particularly preferably at about 6.5%. For achieving a finer dispersion of the particles, an acid, preferably a mineral acid according to step F1), such as hydrochloric acid or nitric acid, can be added prior to the addition of the surface active compound, so that a pH value of 2-6, preferably 3-5 and particularly preferably of about 4 is obtained.

The acid can preferably be selected from mineral acids, such as hydrochloric acid, phosphoric acid, sulfuric acid, bromhydric acid, boric acid or nitric acid. But it is important that an acid, preferably a mineral acid is used which is not irreversibly bound to the particle surface. It has been shown in the experiments that mineral acids are preferred and that amino acids as well as carboxylic acids should be avoided. However, the following acids are basically usable in the inventive method: Sulfonic acid, nitric acid, perchloric acid, methanesulfonic acid, ethanesulfonic acid, hydroxyethanesulfonic acid, ethylenesulfonic acid, p-toluolsulfonic acid, naphtalelesulfonic acid, naphtylaminesulfonic acid, sulfanilic acid and camphorsulfonic acid.

Is the pH of the aqueous solution set by an acid or mineral acid the addition of the at least one surface-active compound is performed according to step F1). The at least one surface-active compound is preferably selected from the group comprising or consisting of salts of saturated and particularly of unsaturated fatty acids. Furthermore, tensides or polymers such as polyvinyl alcohol, polyethylene glycol, polyacrylic acid, dextrane, PLGA, chitosan and polyethylene imine can be used.

Examples of saturated fatty acids are: Acetic acid, propionic acid, butyric acid, caproic acid, capric acid, lauric acid, myristic acid, palmitic acid, margaric acid, stearic acid, arachidic acid, behenic acid and lignoceric acid.

As examples of preferred unsaturated fatty acids or salts thereof any fatty acid can be referred to, such as cis-9-tetradecenoic acid (myristoleic acid), cis-9-hexadecenoic acid (palmitoleic acid), cis-6-octadecenoic acid (petroselinic acid), cis-9-octadecenoic acid (oleic acid), cis-11-octadecenoic acid (vaccenic acid), cis-9-eicosenoic acid (gadoleic acid), cis-11-eicosenoic acid (gondoic acid), cis-13-docosenoic acid (erucic acid), cis-15-tetracosenoic acid (nervonic acid), t9-octadecenoic acid (elaidic acid), t11-octadecenoic acid (trans-vaccenic acid), t3-hexadecenoic acid, 9,12-octadecadienoic acid (linolenic acid), 6,9,12-octadecatrienoic acid (γ-linoleic acid), 8,11,14-eicosatrienoic acid (dihomo-γ-linolenic acid), 5,8,11,14-eicosatetraenoic acid (arachidonic acid), 7,10,13,16-docosatetraenoic acid; 4,7,10,13,16-docosapentaenoic acid, 9,12,15-octadecatrienoic acid (α-linolenic acid), 6,9,12,15-octadecatetraenoic acid (stearidonic acid), 8,11,14,17-eicosatetraenoic acid, 5,8,11,14,17-eicosapentaenoic acid (EPA), 7,10,13,16,19-docosapentaenoic acid (DPA), 4,7,10,13,16,19-docosahexaenioc acid (DHA), 5,8,11-eicosatrienoic acid (mead acid), 9c,11t,13t-eleostearinoic acid, 8t,10t,12c-calendinoic acid, 9c,11t,13c-catalpinoic acid, 4,7,9,11,13,16,19-docosaheptadecanoic acid (stellaheptaenoic acid), taxolic acid, pinolenic acid, sciadonic acid, 6-octadecinoic acid (taririnic acid), t11-octadecen-9-inoic acid (santalbinic or ximeninic acid), 9-octadecinoic acid (stearolinoic acid), 6-octadecen-9-inoic acid (6,9-octadeceninoic acid), t10-heptadecen-8-inoic acid (pyrulinic acid), 9-octadecen-12-inoic acid (crepeninic acid), t7,t11-octadecadien-9-inoic acid (heisterinic acid), t8,t10-octadecadien-12-inoic acid, 5,8,11,14-eicosatetrainoic acid (ETYA) and t8,t10-octadecadien-12-inoic acid. The salts of the fatty acids are preferably formed with alkali and alkaline earth ions.

The mass ratio of the nanoparticles to surface-active compound is preferably 1:0.02 to 1:10, more preferably 1:0.1 to 1:2 and particularly preferably 1:0.5.

After addition of the surface-active compound the suspension according to step G1) is preferably treated with ultrasound for a minimum period of 30 minutes.

The suspension is then stirred for about 2 hours at a temperature preferably in the range from 30° C. to 70° C., more preferably from 50° C. to 60° C., and particularly preferably at 40° C. Then, purification is performed according to step I1). Non-dispersed particles will be separated preferably by centrifugation (1000 U/min).

The dispersion of the particles has to be freed from excess surface-active substance immediately after the coating. This purification can be performed by dialysis or an extraction with diethyl ether. Alternatively, the particles can be centrifuged off using an ultracentrifuge and washed with water and a mixture of water and diethyl ether.

Then the fatty acid-based coating of the particles is exchanged for a silicon-containing biocompatible shell according to steps I1) and J1).

For the exchange of the shell the particles have to be dispersed in a mixture of water and at least one solvent mixable with water according to step I1). As solvents mixable with water are referred to alcohols, polyols, tetrahydrofurans (THF), dimethyl-formamide (DMF), dimethylacetamide, dimethyl sulfoxide (DMSO), acetone, acetic acid, formic acid, methyl-formate ester, ethyl-formate ester, methyl-acetate ester, ethyl-acetate ester and others.

However, alcohols are particularly preferred. The alcohol can preferably be selected from the group comprising or consisting of methanol, ethanol, propanol, isopropanol and ethylene glycol, wherein ethanol is preferred.

The mixture ratio of water and alcohol and water and ethanol, respectively, is preferably 1:1 to 1:5, and particularly preferred 1:3, so that the removal of the fatty acid shell and the exchange by the silicon-containing shell can be performed in parallel.

Further, it is preferred if the mixture of alcohol and water contains 1-5% by weight, further preferred 1-3% by weight and particularly preferred 1.5% by weight of an amine, preferably of a primary amine, and particularly preferably of ammonia.

Shortly after the addition of the dispersion of the nanoparticles to the mixture of solvents, particularly to the mixture of alcohol and water and preferably to the mixture of water and ethanol according to step I1) a suitable alkoxysilane has to be added. The addition of the alkoxysilane should occur under ultrasonic treatment. Suitable alkoxysilanes are all tetraalkoxysilanes, such as tetramethoxysilane and tetraethoxysilane, and trialkoxysilanes, dialkoxysilanes, and monoalkoxysilanes, which have preferably a functional group coupled by a Si—C bond, such as an amino group, a thiol group and/or an epoxy group.

For the exchange of the shell to run smoothly, the molar ratio of iron and alkoxysilane should be 1:1 to 1:5, and preferably 1:3.

After the addition of the reactants the dispersion is treated with ultrasound for 1-8 hours, preferably for 3-5 hours and particularly preferably for 4 hours, according to step J1). Then the purification of the particles is performed preferably by dialysis against water. Alternatively, the purification can be performed by centrifuging the particles off at a high g-value and washing of the precipitate with ultrapure water.

Moreover, the present invention refers to particles and preferably nanoparticles which can be obtained with the method disclosed herein.

The inventive iron-containing particles themselves are ferromagnetic, ferrimagnetic or superparamagnetic. Such particles or nanoparticles can be warmed by an alternating magnetic field. A warming of the tissue containing the particles or the nanoparticles to over 50° C. is possible, because the particles or nanoparticles have high SAR values.

The iron-containing particles possess a minimum SAR value of 18, preferably of 20 and particularly preferably of 22 mW/mg Fe at a field strength of 6 kA/m.

The particles have preferably a diameter of less than 500 nm. The nanoparticles have preferably an average diameter of 20 nm, or are preferably in the size-range of 1-100 nm and particularly preferably in the size-range of 15-30 nm.

The stable silicon-containing shell of the nanoparticles has a thickness between 0.5 and 10 nm, preferably of 3 nm.

The silicon-containing shell can be functionalized by further alkoxysilanes to modify the properties of the particles. These are preferably trialkoxysilanes bearing a functional group coupled by a Si—C bond. Examples therefor are (3-acryloxypropyl)trimethoxysilane, triethoxysilyl-butyraldehyde, 3-amino-propyltriethoxysilane, and 3-isocyanato-propyltriethoxysilane. The trialkoxysilanes can also bear Si—C-bonded polyethylene glycol side chains of different lengths. As an example for this serves 2-[methoxy (polyethylenoxy)propyl]trimethoxysilane.

The iron-containing particles may be used in the field of medicine, and e.g. be injected in form of an aqueous solution. The iron-containing particles may be used for the treatment and prophylaxis of proliferative diseases, cancer, tumors, rheumatism, arthritis, arthrosis, and bacterial infections.

Furthermore, the present invention refers to pharmaceutical compositions containing the nanoparticles described herein, as well as to the use of the nanoparticles for the preparation of such pharmaceutical compositions.

These pharmaceutical compositions are in particular solutions for infusion or injection. Such solutions of the nanoparticles in, for instance, physiological saline are suitable for interstitial or intra-tumoral application. Further, an intra-arterial or an intravenous application allows a systemic treatment option affecting the whole body for nonsolid and/or metastasis-forming types of tumors.

Further preferred pharmaceutical compositions are powder, inhalation powder and lyophilisates containing the iron-containing particles described herein.

The nanoparticles and pharmaceutical compositions will be used preferably for the treatment as well as for the prophylaxis of diseases which are characterized by degenerated cell species or exogenous cells and for which the feature of the nanoparticles to discriminate between exogenous or degenerated cells and the body's own healthy cells can be used. As being degenerated cells are considered particularly cancer cells or cells with an impaired proliferation as well as stenotic or restenotic tissue. Examples for exogenous cells are in particular bacteria.

Therefore, the nanoparticles and the pharmaceutical compositions containing the nanoparticles will be used for the prophylaxis and treatment of tumors, carcinomas and cancer.

Examples for kinds of cancers and tumors for which the inventive nanoparticles can be used are: Adenocarcinomas, choroidal melanoma, acute leukemia, acoustic neurinoma, ampullary carcinoma, anal carcinoma, astrocytomas, basal cell carcinoma, pancreatic cancer, connective tissue tumor, bladder cancer, bronchial carcinoma, non-small cell bronchial carcinoma, breast cancer, Burkitt's lymphoma, corpus carcinoma, CUP syndrome, cancer of the large intestine, cancer of the small intestine, tumors of the small intestine, ovarian cancer, endometrial carcinoma, ependymoma, epithelial cancers, Ewing tumors, gastrointestinal tumors, gall bladder cancer, gall carcinomas, uterine cancer, cervical cancer, glioblastomas, gynecological tumors, tumors of ear, nose and throat, hematological neoplasias, hairy cell leukemia, urethral cancer, skin cancer, brain tumors (gliomas), brain metastases, testicular cancer, hypophysis tumor, carcinoids, Kaposi's sarcoma, laryngeal cancer, germ cell tumor, bone cancer, colorectal carcinoma, head and neck tumors (tumors situated in the region of the neck, nose and ears), colon carcinoma, craniopharyngiomas, cancer in the area of the mouth and on the lip, liver cancer, liver metastases, leukemia, tumor of the eyelid, lung cancer, malignant lymphoma (Hodgkin/Non-Hodgkin), lymphomas, stomach cancer, malignant melanoma, malignant neoplasm, malignomas of the gastrointestinal tract, breast carcinoma, rectal cancer, medulloblastomas, melanoma, meningiomas, Hodgkin's disease, mycosis fungoides, nose cancer, neurinoma, neuroblastoma, kidney cancer, renal cell carcinoma, Non-Hodgkin's lymphomas, oligodendroglioma, esophageal carcinoma, osteolytic tumors and osteoblastic tumors, osteosarcoma, ovarian carcinoma, pancreatic carcinoma, penile carcinoma, plasmacytoma, squamous cell carcinoma of the head and the neck, prostate cancer, throat cancer, rectal carcinoma, retinoblastoma, vaginal cancer, thyroid carcinoma, Schneeberg lung cancer, esophageal cancer, spinocellular carcinoma, T-cell lymphoma (Mycosis fungoides), thymoma, tube carcinoma, eye tumors, urethral carcinoma, urological tumors, urothelial carcinoma, vulvar carcinoma, wart appearance, soft tissue tumors, soft tissue sarcoma, Wilms tumor, cervical carcinoma and tongue cancer.

Solid tumors are particularly preferred. Further preferred are prostate carcinomas, brain tumors, sarcomas, cervical carcinomas, ovarian carcinomas, breast carcinomas, bronchial carcinomas, melanomas, head and neck tumors, esophageal carcinomas, rectal carcinomas, pancreatic, bladder and renal carcinomas, and metastases in the liver, in the brain and in the lymph nodes.

Particularly preferred are the application and the usage of the inventive nanoparticles in combination with conventional hyperthermia, radiation therapy and/or in combination with the conventional chemotherapy.

Further it could be found that the inventive magnetic and preferably superparamagnetic particles increase the activity of anticancer agents and, additionally, reduce their side effects. Thus, the particles produced will be used preferably in combination with anticancer drugs, i.e. with cytotoxic and/or cytostatic compounds, i.e. chemical compounds with cytotoxic and/or cytostatic properties. Examples for anticancer drugs include, amongst others, alkylating agents, antibiotics with cytostatic properties, antimetabolites, microtubule inhibitors and topoisomerase inhibitors, platinum-containing compounds and other cytostatics, such as asparaginase, tretinoin, alkaloids, podophyllotoxins, taxanes and Miltefosine®, hormones, immunomodulators, monoclonal antibodies, signal transductors (molecules for signal transduction), kinase inhibitors and cytokins.

Examples for alkylation agents include amongst others chlorethamine, cyclophosphamide, trofosfamide, ifosfamide, melphalan, chlorambucil, busulfan, thiotepa, carmustine, lomustine, dacarbazine, procarbazine, temozolomide, treosulfan, estramustine and nimustine.

Examples for antibiotics having cytostatic properties are daunorubicin as well as liposomal daunorubicin, doxorubicin (adriamycin), dactinomycin, mitomycin C, bleomycin, epirubicin (4-epi-adriamycin), idarubicin, dactinomycin, mitoxantrone, amsacrine and actinomycin D.

Methotrexate, 5-fluorouracil, 6-thioguanine, 6-mercaptopurine, fludarabine, cladribine, pentostatin, gemcitabine, cytarabine, azathioprine, raltitrexed, capecitabine, cytosine arabinoside, thioguanine and mercaptopurine can be mentioned as examples for antimetabolites (antimetabolic drugs).

To the class of alkaloids and podophyllotoxins belong, amongst others, vincristine, vinblastine, vindesine, etoposide as well as teniposide. Furthermore, platinum-containing compounds can be used. Cisplatin, carboplatin and oxaliplatin are examples for compounds containing platinum. Among the microtubule inhibitors are counted, for example, alkaloids such as vinca alkaloids (vincristine, vinblastine, vindesine, vinorelbine) and paclitaxel (Taxol®) as well as derivatives of paclitaxel. Examples for topoisomerase inhibitors include etoposide, teniposide, camptothecin, topotecan and irinotecan.

Paclitaxel and docetaxel are examples for taxane compounds and among the other cytostatic agents (other cytostatics) are counted, for example, hydroxycarbamide (hydroxyurea), imatinib, Miltefosine®, amsacrine, topotecan (topoisomerase-I inhibitor), pentostatin, bexarotene, tretinoin and asparaginase. Representatives of the compound class of monoclonal antibodies are amongst others trastuzumab (also known as Herceptin®), alemtuzumab (also known as MabCampath®) and rituximab (also known as MabThera®). Representatives of kinase inhibitors are Sorafenib (Nexavar®) and Sunitinib (Sutent®). Examples for hormones are glucocorticoids (prednisone), estrogens (fosfestrol, estramustine), LHRH (buserelin, goserelin, leuprorelin, triptorelin), flutamide, cyproterone acetate, tamoxifen, toremifen, aminoglutethimide, formestane, exemestane, letrozole and anastrozole. Among the classes of immunomodulators, cytokines, antibodies and signal transduces are counted interleukin-2, interferon-α, erythropoietin, G-CSF, trastuzumab (Herceptin®), rituximab (MabThera®), gefitinib (Iressa®), ibritumomab (Zevalin®), levamisole as well as retinoids.

Thus, the present invention also refers to combinations of the particles produced as described herein with at least one anticancer agent, such as actinomycin D, aminoglutethimide, amsacrin, anastrozole, antagonists of purine and pyrimidine bases, anthracyclins, aromatase inhibitors, asparigi- nase, anti-estrogens, bexaroten, bleomycin, buserelin, busulfan, camptothecin derivatives, capecitabin, carboplatin, carmustin, chlorambucil, cisplatin, cladribin, cyclophosphamid, cytarabin, cytosine arabinosid, alkalyting cytostatics, dacarbazine, dactiomycin, docetaxel, doxorubicin (adriamycin), doxorubicin lipo, epirubicin, extramustin, etoposid, exemestan, fludarabin, fluorouracil, folic acid antagonists, formestan, gemcitabine, glucocorticoids, goselerin, hormones and hormone antagonists, hycamtin, hydroxyurea, idarubicin, ifosfamid, imatinib, irinotecan, letrozol, leuprorelin, lomustin, melphalan, mercaptopurin, methotrexat, miltefosin, mitomycine, mitotic inhibitors, mitoxantron, nimustine, oxaliplatin, paclitaxel, pentostatin, procarbazine, tamoxifen, temozolomide, teniposide, testolactone, thiotepa, thioguanine, topoisomerase inhibitors, topotecan, treosulfan, tretinoin, triptorelin, trofosfamide, vinblastine, vincristine, vindesine, vinorelbine, cytostatically active antibiotics and pharmaceutical compositions containing the aforementioned combinations.

The aforementioned drugs can be used not only in combinations with the inventive particles but also be bound covalently to the particles, preferably nanoparticles, to be imported yet more efficiently into the cancer cells.

Thus, a further aspect is directed to particles obtainable according to the inventive method, wherein a therapeutically active substance is bound covalently to a particle or nanoparticle. The therapeutically active substances can be selected from anti-proliferative, anti-migrative, anti-angiogenic, anti-thrombotic, anti-inflammatory, antiphlogistic, cytostatic, cytotoxic, anti-coagulative, antibacterial, antiviral, and/or anti-mycotic drugs, wherein anti-proliferative, anti-migrative, anti-angiogenic, cytostatic and/or cytotoxic drugs as well as nucleic acids, amino acids, peptides, proteins, carbohydrates, lipids, glycoproteins, glycanes or lipoproteins with anti-proliferative, anti-migrative, anti-angiogenic, anti-thrombotic, anti-inflammatory, antiphlogistic cytostatic, cytotoxic, anti-coagulative, antibacterial, antiviral and/or anti-mycotic properties are preferred. Furthermore, these substances can also contain radiosensitizers or sensitizers or enhancers of other conventional methods for cancer treatment which are also combined or contain such sensitizers.

The coupling of the therapeutically active substance can be performed, for instance, via hydroxyl groups, amino groups, carbonyl groups, thiol groups or carboxylic groups, depending which functional group is carried by the respective drug. Hydroxyl groups are preferably bound as esters, acetals or ketals, thiol groups preferably as thioesters, thioacetals or thioketals, amino groups preferably as amides and partly also as imines (Schiff bases), carboxylic groups preferably as esters or amide, and carbonylic groups preferably as ketals. Further, the functionalizing of the surface of the nanoparticles is known, so that using the known methods aminogroups, hydroxygroups, carboxylic groups or carbonyl groups can be produced at the surface of the nanoparticles.

A further coating of the activatable nanoparticle-drug-conjugates (e.g. by polymers) as described in patent specification WO 98/58673 is also possible and can be used to improve the biological properties of the particle-drug-conjugates. Further molecules conferring targeting properties to the whole construct can also be coupled (e.g. polyclonal antibodies, monoclonal antibodies, humanized antibodies, humane antibodies, chimeric antibodies, recombinant antibodies, bispecific antibodies, antibody fragments, aptamers, Fab-fragments, Fc-fragments, peptides, peptidomimetics, gap-meres, ribozymes, CpG-oligomers, DNA-zymes, riboswitches, or lipids). It is essential that all further modifications do not impede the activatable release of the therapeutically active substance at the target site.

It is further preferred that the therapeutically active substance is not bonded directly to the nanoparticle, but immobilized using a linker molecule. As linker can serve diverse molecules with up to 50 carbon atoms, provided the linker contains a group which can be cleaved thermally, photochemically or enzymatically, an acid-labile group or a group which is easy to be detached by other means. A bond within the linker molecule and/or the bond of the linker to the drug and/or the bond of the linker to the surface of the nanoparticle have to be cleavable directly or indirectly by the effect of the alternating magnetic field. An indirect cleavage is given if, for instance, enzymes such as peptidases, esterases or hydrolases are stimulated, or if their activity or expression is enhanced, by the alternating magnetic field at the target site, e.g. in the cancer cell, and if these enzymes can then perform the afore-mentioned cleavage. Furthermore, an indirect cleavage can also take place using magnetic nanoparticles if these are warmed up by the alternating magnetic field and a thermally labile group is cleaved thereby. It is also possible to increase the pH at the target location by the effect of the alternating magnetic field to cleave subsequently the acid-labile bonds within the linker molecule.

As an enzymatically cleavable group within or at the linker molecule the amide group has to be mentioned. Groups cleavable thermally or by an acid comprise, for example, phosphate groups, thiophosphate groups, sulfate groups, phosphamide groups, carbamate groups or imine groups.

The linker molecule can also be a nucleic acid molecule, a polypeptide, a peptide-nucleic acid, an aptamer, DNA, RNA, a leucin zipper, an oliconucleotide, biotin, avidin, streptavidin, a hapten-antibody-bridge or a biotin-avidin-bridge.

The drug does not have to be bound covalently to the linker, but can also be bound ionically or by hydrogen bonds, or be intercalated or complexed.

The diverse possibilities of bonding a therapeutically active substance, such as an anticancer agent, a monoclonal antibody, an aptamer, a nucleic acid, an amino acid, a peptide, a protein, a carbohydrate, a lipid, a glycoprotein, a glycan, a lipoprotein, or an anti-proliferative, an anti-migrative, an anti-angiogenic; an anti-thrombotic, an anti-inflammatory, an antiphlogistic, a cytostatic, a cytotoxic, an anti-coagulative, an anti-bacterial, an anti-viral, or an anti-mycotic drug to microparticles and nanoparticles, are described in detail in WO2006108405A.

Thus, the inventive method can comprise a further step L1), which refers to the bonding of anticancer agent, a monoclonal antibody, an aptamer, a nucleic acid, an amino acid, a peptide, a protein, a carbohydrate, a lipid, a glycoprotein, a glycan, a lipoprotein, or an anti-proliferative, an anti-migrative, an anti-angiogenic, an anti-thrombotic, an anti-inflammatory, an antiphlogistic, a cytostatic, a cytotoxic, an anti-coagulative, an anti-bacterial, an anti-viral, or an anti-mycotic drug to the particles according to step K1).

Furthermore, it is also possible to bind the drugs to the surface of the nanoparticles by adsorption and to cover them with a barrier layer which mostly prevents the release of the drug until the barrier layer is modified or particularly degraded by the effect of the alternating magnetic field in such a way that the release of the drug can occur.

General Synthesis Specification for the Production of the Inventive Particles

Step A1)
For the production of particle seeds in an organic solvent LM1 with a boiling point of about 200° C. to about 400° C., 0.02 mol of an iron-containing compound A and 100 ml of the solvent are given into a glass flask.

Step A2)
One of the additives described herein can now be added optionally at an amount of 0.008 to 0.05 mol.

Step B1)
The solution is heated for a minimum period of 10 minutes and preferably for 1 hour to a temperature between 50° C. and 350° C., which is about 50° C. below the subsequent reaction temperature.

Step B2)
A further additive as well as a further iron-containing compound B can now be added optionally.

Step C1)
The obtained mixture is heated in a three-necked-flask with reflux cooling under passing over protective gas up to the boiling temperature of the respective solvent LM1 or LM2 which should be at least 50° C. higher than the temperature of the heating phase according to step B1), and is kept at this temperature for a minimum period of about 1 hour.

Step C2)
The obtained iron oxide particles can now be oxidized optionally.

Step D1)
Now the purification of the particles is performed by centrifugation, washing and preferably Soxhlet extraction.

Step D1*)
At least one tempering phase of the iron oxide nanoparticles can be performed optionally.

Step D2)
So far this has not been done yet the iron oxide nanoparticles can now be oxidized optionally.

Step D2*)

At least one tempering phase of the iron oxide nanoparticles can be performed optionally.

Step E1)

For the dispersion or the suspension of the purified particles they will be re-suspended in water with a neutral pH or in an acid aqueous solution, preferably containing a mineral acid. The acid concentration is 0.002 to 0.1 M. For supporting the dispersion or suspension ultrasonic treatment can be performed.

Step E2)

So far this has not been done yet the iron oxide nanoparticles can now be oxidized optionally.

Step F1)

Now the addition of a surface-active compound in an amount of 3 to 8 mmol is effected.

Step F2)

So far this has not been done yet the iron oxide nanoparticles can now be oxidized optionally.

Step G1)

Optionally it will be stirred, preferably for 1 to 2 hours at 50° C. to 90° C. Under stirring follows the ultrasound treatment for 1 to 3 hours.

Step G2)

So far this has not been done yet the iron oxide nanoparticles can now be oxidized optionally.

Step H1)

Now the purification of the obtained particles is effected by centrifugation, washing, extraction and/or dialysis, depending on which method or combination of methods is better.

Step H2)

So far this has not been done yet the iron oxide nanoparticles can now be oxidized optionally.

Step I1)

The obtained particles will be re-suspended in a mixture of water and alcohol (1:1 to 5:1), which optionally contains an amine and preferably ammonia in low concentrations.

Step I2)

So far this has not been done yet the iron oxide nanoparticles can now be oxidized optionally.

Step J1)

Now the addition of an alkoxysilane is effected in an amount of 0.04 to 0.08 mol.

Step J2)

So far this has not been done yet the iron oxide nanoparticles can now be oxidized optionally.

Step K1)

Now the purification of the obtained particles is effected by centrifugation, dialysis, washing, and/or re-dispersion, depending on which method or combination of methods is better.

Step K2)

So far this has not been done yet the iron oxide nanoparticles can now be oxidized optionally.

Step L1)

Optionally the binding of drugs to the iron oxide nanoparticles can be performed now.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

For producing particle seeds in diethylene glycol-dibutyl ether 0.3 g of iron pentacarbonyl were dissolved in 50 ml of diethylene glycoldibutyl ether in a glass flask. 1.7 g of oleic acid were added to the solution. The solution was heated to 150° C. for 1 hour.

Example 2

For the production of particle seeds in polyglycol DME 500 (company Clariant) 8 g of iron(III) oleate were dissolved in 50 ml polyglycol DME 500 in a glass flask. 1.5 g of oleic acid were added to the solution. The solution was heated to 120° C. for 30 min.

Example 3a

For the production of iron oxide nanoparticles the solutions of examples 1-2 were heated in a three-necked-flask with reflux condensation under conduction of protective gas (argon) up to the boiling temperature of the respective solvent and kept at this temperature for a minimum period of 1 hour. Thereby the solution turned red. After cooling down the particles were oxidized over night by conduction of atmospheric oxygen.

Example 3B

For the production of iron oxide nanoparticles the solutions of examples 1-2 were heated in a three-necked-flask with reflux cooling under conduction of a protective gas (argon) up to the boiling temperature of the respective solvent and kept at this temperature for a minimum period of 1 hour. Herein the solution turned black.

Example 4

The particles of example 3 were centrifuged off at high g-values and washed with ethanol. 500 mg of the washed product were weighted in an extraction thimble (603 g company Whatman) and placed in a Soxhlet apparatus. 200 ml of the extractant ethanol were filled into the recovery flask of the Soxhlet apparatus. The extractant was heated up to its boiling point. The continuing extraction was carried out over 8 hours and included about 16 extraction cycles. Thereby the ethanol solution turned yellowish. After finishing the extraction thimble was removed and the powder transferred into a Schlenkflask and dried in vacuum for 1 h.

Example 5

For the dispersion of the particles after the extraction 0.5 g of the nanoparticle powder from example 4 were suspended in 20 ml of 0.01 M HCl. The nanoparticles were then treated with ultrasound for 30 minutes. Then 0.5 g solid sodium oleate were added.

Step G1:

Then it was stirred at 70° C. for 1.5 hours, followed by an ultrasonic treatment under stirring for 2 hours. After successful dispersing the dispersion was centrifuged at low g-values to separate the non-dispersed particles. Alternatively, the remaining dispersion was washed to remove excessive sodium oleate. This is performed by centrifugation at high g-values and washing with diethyl ether and re-dispersing in water. Alternatively, an extraction can be performed with diethyl ether or a dialysis. For complete re-dispersing the dispersion was treated with ultrasound.

Example 6

3.3 ml of a particle dispersion according to example 5 (0.97 mol/1 Fe) and 2.14 ml of tetraethoxysilane were added to 120 ml of a mixture of water and ethanol (3:1) and of 1.5% by weight of ammonia. During the addition the dispersion was stirred and then treated with ultrasound for 6 hours. The dispersion was purified by centrifugation and re-dispersing in water.

Example 7 (Tempering Phase)

The particles obtained in example 4 were suspended in 200 ml of diethyleneglycoldibutylether. Then they were fumigated with air at 80° C. for 12 hours and then boiled under reflux for 8 hours (boiling point at about 256° C.). The suspension was then cooled down to room temperature slowly (within 8 hours). This procedure was repeated twice.

The (tempered) particles obtained that way were washed and suspended in 20 ml of 1M $HNO_3$. Then 0.3 mmol iron nitrate ($Fe(NO_3)_3.9H_2O$) were added and boiled under reflux for 1 hour (100° C.). The particles were washed 3 times with 100 ml water each time.

Then the particles were coated in analogy to examples 4-6.

Example 8A (with Oxidation/without Fumigation with Air)

For the production of iron oxide nanoparticles in ethylene glycol 0.1 mol $FeCl_3.6H_2O$ and 0.2 mol $FeCl_3$ (anhydrous), 50 g sodium acetate and 195 g diaminohexane were dissolved in 900 ml of ethylene glycol and heated up to 60° C. for one hour.

Then the solution was heated up to the boiling point within 30 minutes. The boiling temperature was kept for 6 hours. The formed dispersion was cooled down slowly to room temperature.

The particles were washed with a mixture of ethanol and water for three times.

Then the particles were re-suspended in 900 ml of ethylene glycol. The suspension was heated to the boiling point of ethylene glycol and kept at this temperature for 24 hours.

After cooling down the particles were washed with a mixture of water and ethanol and re-suspended in 900 ml of 1M $HNO_3$. Then 450 ml of a 0.7 M solution of iron nitrate ($Fe(NO_3).9 H_2O$) were added and boiled under reflux for one hour 100° C.). The particles were washed three times with 500 ml of water each time.

These particles were coated in analogy to examples 4-6.

Example 8B (without Oxidation with Fumigation with Air)

For the production of iron oxide nanoparticles in ethylene glycol 0.1 mol $FeCl_3 6.H_2O$ and 0.2 mol $FeCl_3$ (anhydrous), 50 g sodium acetate and 195 g diaminohexane were dissolved in 900 ml of ethylene glycol and heated to 60° C. for one hour.

Then the solution was heated to the boiling point within 30 minutes. The boiling temperature was kept for 6 hours. The formed dispersion was slowly cooled down to room temperature.

The particles were washed with a mixture of ethanol and water for three times. Then the particles were resuspended in 900 ml of ethylene glycol and fumigated with atmospheric oxygen. The suspension was heated up to the boiling point of ethylene glycol and kept at this temperature for 24 hours.

After cooling down the particles were washed with a mixture of water and ethanol and re-suspended in water.

These particles were coated in analogy to examples 4-6.

Example 8C (with Oxidation 1 with Fumigation with Air)

For the production of iron oxide nanoparticles in ethylene glycol 0.1 mol $FeCl_3.6H_2O$ and 0.2 mol $FeCl_3$ (anhydrous), 50 g sodium acetate and 195 g diaminohexane were dissolved in 900 ml of ethylene glycol and heated up to 60° C. for one hour.

Then the solution was heated up to the boiling point within 30 minutes. The boiling temperature was kept for 6 hours. The formed dispersion was cooled down slowly to room temperature.

The particles were washed with a mixture of ethanol and water for three times.

Then the particles were re-suspended in 900 ml of ethylene glycol and fumigated with atmospheric oxygen. The suspension was heated up to the boiling point of the ethylene glycol and kept at this temperature for 24 hours.

After cooling down the particles were washed with a mixture of water and ethanol and re-suspended in 900 ml of 1M $HNO_3$. Then 450 ml of a 0.7 M iron nitrate solution ($Fe(NO_3)_3.9H_2O$) were added and boiled under reflux for one hour (100° C.). The particles were washed three times with 500 ml of water each time.

These particles were coated in analogy to examples 4-6.

Example 8D (without Oxidation/without Fumigation with Air)

For the production of iron oxide nanoparticles in ethylene glycol 0.1 mol $FeCl_3. 6H_2O$ and 0.2 mol $FeCl_3$ (anhydrous), 50 g sodium acetate and 195 g diaminohexane were dissolved in 900 ml of ethylene glycol and heated up to 60° C. for one hour.

Then the solution was heated up to the boiling point within 30 minutes. The boiling temperature was kept for 6 hours. The formed dispersion was cooled down slowly to room temperature.

The particles were washed with a mixture of ethanol and water for three times.

Then the particles were re-suspended in 900 ml of ethylene glycol. The suspension was heated up to the boiling point of ethylene glycol and kept at this temperature for 24 hours. After cooling down the particles were washed with a mixture of water and ethanol and re-suspended in water.

These particles were coated in analogy to examples 4-6.

Example 9

For the production of iron oxide nanoparticles a solution of 96 g of sodium hydroxide and 680 ml of oleic acid in 2000 ml of methanol was added to a solution of 216 g Fe(III) chloride-hexahydrate in 500 ml of methanol. The resulting solid was washed with methanol and dissolved in diethyl ether. Then it was extracted with water several times. The solid was precipitated with acetone, washed and dried under vacuum.

75 g of this solid were dissolved in 250 ml of trioctylamine and were heated to 120° C. for one hour.

Then the solution was heated in an autoclave to a temperature of 380° C. within 30 minutes. This temperature was kept for 4 hours. The formed dispersion was slowly cooled down to room temperature.

The particles were washed with a mixture of ethanol and water for three times.

Then the particles were suspended in 300 ml of diethylene glycol dibutyl ether and fumigated with atmospheric oxygen. The suspension was heated in the autoclave to a temperature of 300° C. and kept at this temperature for 24 hours.

These particles were oxidized like in example 8C and then coated in analogy to examples 4-6.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. Nanoparticles, wherein the nanoparticles are biocompatible and have a specific absorption rate (SAR) value of 10-40 W per g Fe at a field strength of 4 kA/m and at a frequency of an alternating magnetic field of 100 kHz, wherein the nanoparticles comprise iron and have a silicon-containing core shell, wherein the silicon-containing core shell has a thickness of between 0.5 nm to 10 nm, and wherein the nanoparticles are made by thermal decomposition.

2. The nanoparticles according to claim 1, wherein the silicon-containing core shell is functionalized by alkoxysilanes.

3. The nanoparticles according to claim 1, wherein the silicon-containing core shell has a thickness of 1 to 6 nm.

4. The nanoparticles according to claim 1, wherein the nanoparticles are ferromagnetic, ferrimagnetic or superparamagnetic.

5. The nanoparticles according to claim 1, wherein the nanoparticles have a specific absorption rate (SAR) value of 20-40 W per g Fe at a field strength of 4 kA/m and at a frequency of an alternating magnetic field of 100 kHz.

6. Nanoparticles according to claim 1, wherein the nanoparticles are not dispersible in non-polar solvents and dispersible in water.

7. Nanoparticles according to claim 1, wherein the nanoparticles have a diameter of less than 500 nm.

8. Nanoparticles according to claim 2, wherein the silicon-containing shell is functionalized by further alkoxysilanes.

9. Nanoparticles according to claim 8, wherein the further alkoxysilanes are trialkoxysilanes.

10. Nanoparticles according to claim 9, wherein the trialkoxysilanes are
   (i) bearing a functional group coupled by a Si—C bond, preferably selected from the group consisting of (3-acryloxypropyl)trimethoxysilane, triethoxysilyl-butyraldehyde, 3-amino-propyltriethoxysilane, and 3-isocyanato-propyltriethoxysilane; or
   (ii) bearing Si—C-bonded polyethylene glycol side chains of different lengths, preferably 2-[methoxy (polyethylenoxy)propyl]trimethoxysilane.

11. A composition comprising the nanoparticles according to claim 1.

12. A pharmaceutical composition comprising the nanoparticles according to claim 1.

13. The pharmaceutical composition according to claim 12 in form of an infusion solution, an injection solution, a powder, inhalation powder or a lyophilisate.

14. The nanoparticles of claim 1, wherein the silicon-containing core shell has a thickness of 2 to 4 nm.

15. The nanoparticles of claim 1, wherein the silicon-containing core shell has a thickness of 3 nm.

16. The nanoparticles of claim 5, wherein the nanoparticles have a specific absorption rate (SAR) value of 25-40 W per g Fe at a field strength of 4 kA/m and at a frequency of an alternating magnetic field of 100 kHz.

17. The nanoparticles of claim 5, wherein the nanoparticles have a specific absorption rate (SAR) value of 30-40 W per g Fe at a field strength of 4 kA/m and at a frequency of an alternating magnetic field of 100 kHz.

18. The nanoparticles of claim 7, wherein the nanoparticles have a diameter of 1 to 100 nm.

19. The nanoparticles of claim 7, wherein the nanoparticles have a diameter of 15 to 30 nm.

* * * * *